US00PP14021P3

(12) United States Plant Patent
Zipperer, III

(10) Patent No.: US PP14,021 P3
(45) Date of Patent: Jul. 29, 2003

(54) GLADIOLUS PLANT NAMED 'PRINCESS LEE'

(76) Inventor: John O. Zipperer, III, 13590 Brynwood La., Ft. Myers, FL (US) 33912

( * ) Notice: Subject to any disclaimer, the term of this patent is extended or adjusted under 35 U.S.C. 154(b) by 0 days.

(21) Appl. No.: 09/877,573

(22) Filed: Jun. 8, 2001

(65) Prior Publication Data

US 2002/0002723 P1 Jan. 3, 2002

(30) Foreign Application Priority Data

Jun. 9, 2000 (EP) ..... 2000/0893

(51) Int. Cl.[7] ..... A01H 5/00
(52) U.S. Cl. ..... Plt./301
(58) Field of Search ..... Plt./301

(56) References Cited

PUBLICATIONS

U.S. patent application Ser. No. 09/745,086, Zipperer, III, filed on Dec. 20, 2000.*
U.S. patent application Ser. No. 09/742,726, Zipperer, III, filed on Dec. 20, 2000.*
U.S. patent application Ser. No. 09/877,571, Zipperer, III, filed on Jun. 8, 2001.*
U.S. patent application Ser. No. 09/877,572, Zipperer, III, filed on Jun. 8, 2001.*
U.S. patent application Ser. No. 09/877,574, Zipperer, III, filed on Jun. 8, 2001.*
U.S. patent application Ser. No. 09/877,575, Zipperer, III, filed on Jun. 8, 2001.*
U.S. patent application Ser. No. 09/918,662, Zipperer, III, filed on Jul. 31, 2001.*
U.S. patent application Ser. No. 09/918,660, Zipperer, III, filed on Jul. 31, 2001.*
U.S. patent application Ser. No. 09/918,663, Zipperer, III, filed on Jul. 31, 2001.*

* cited by examiner

*Primary Examiner*—Bruce R. Campell
*Assistant Examiner*—Anne Marie Grünberg
(74) *Attorney, Agent, or Firm*—Laura G. Barrow; Hahn, Loeser + Parks LLP

(57) ABSTRACT

A new and distinct gladiolus variety, designated 'Princess Lee' is shown and described. The variety has straight, strong stems, a large bloom size, slow to open, and has good resistance to attack by insects and foliar diseases.

4 Drawing Sheets

The present invention comprises a new and distinct variety of a *Gladiolus l.* referred to by the variety name 'Princess Lee'.

BRIEF DESCRIPTION OF THE PHOTOGRAPHS

ASEXUAL REPRODUCTION

The new variety was originated by the Applicant in a controlled proprietary breeding program in Ft. Myers, Fla. wherein selected gladiolus varieties were crossed. (The provisional breeder's designation "48-24" was used in a related application for a Community plant variety right filed earlier in the European Union Community Plant Variety Office). The female parent was a gladiolus variety named 'Dr. Magie,' an unpatented variety characterized in part by having a small pink bloom, a short stem having a short flower head, and high resistance to Fusarium fungi species. The male parent was an unpatented gladiolus variety named 'White Prosperity,' a short-headed, light-stemmed white variety (when grown during short day seasons) that prefers long day lengths (i.e. 14 to 17-hour days). The seeds were planted in Ft. Myers, Fla., and the selection of 'Princess Lee' variety was made in Spring 1988. Asexual reproduction of the 'Princess Lee' variety was achieved by collecting cormels from the first corm and growing said cormels to maturity in Ft. Myers. All subsequent asexual reproductions of the 'Princess Lee' variety remain true to the original variety type.

BOTANICAL DESCRIPTION

The accompanying color photographs show the inflorescence and various stages of blooming of the 'Princess Lee' variety plant (age about 76 days).

The following botanical description, except for color and stem diameter, of the 'Princess Lee' variety was observed when the plant was 90 days old grown under the following conditions in Ecuador:

1) Twelve-hour daylight days with high light intensity;

2) Temperatures: 58–60° F. (low's) and 69–75° F. (high's);

3) Humidity: 50–55%

4) Rainfall: 2–3 inches/month.

All color descriptions with respect to parts of the variety, where color is a distinguishing feature, are made to The Royal Horticultural Society Colour Chart (R.H.S.), except where terms of ordinary usage and dictionary meaning are used. Color observations with respect to The R.H.S. Colour Chart were made in the Netherlands under similar environmental conditions as described above, but at increased day lengths of 12 to 17 hours and 50% to 65% humidity.

The spike of the plant is about 123 cm and comprises 16 florets when grown from #1 size corms (1.5 inch) in Ecuador. The color of the stem is Yellow Green 144C on the backside between the flower buds, and the stem diameter is about 1.2 cm in South Florida in December. The head length is about 56 cm. It should be noted, however, that various factors will affect spike length, including temperature (larger spikes occur in cooler weather), irrigation, light intensity, fertilization, soil type (larger spikes occur in heavy soils versus sandy soil), and bulb size (larger bulbs result in larger spikes). The leaf color of the 'Princess Lee' variety is Green Group 137B on both sides. The leaf size is about 65 cm (length) by 4 cm (width).

Figure 1:
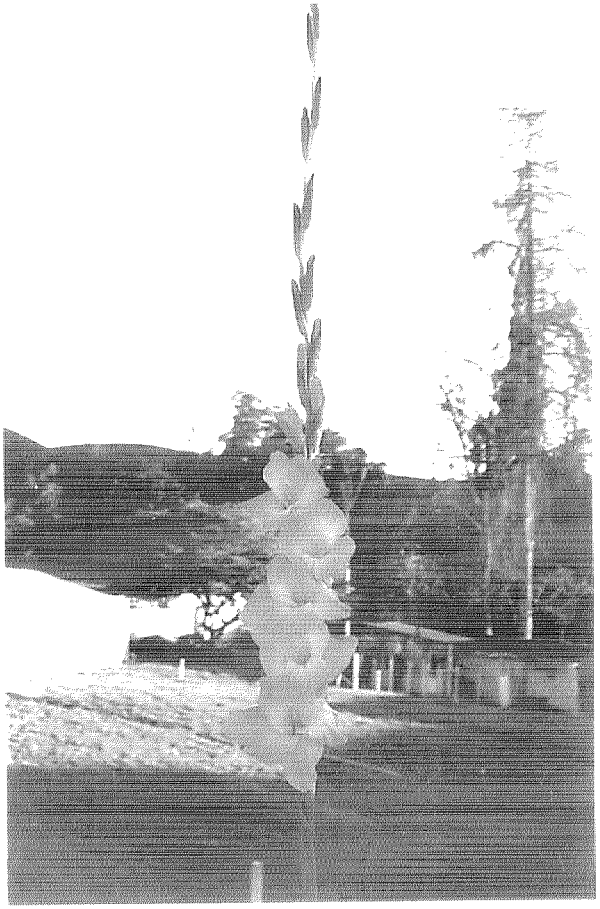
FIGS. 1 and 2 are photographs of a 'Princess Lee' variety plant in bloom.
Figure 2:
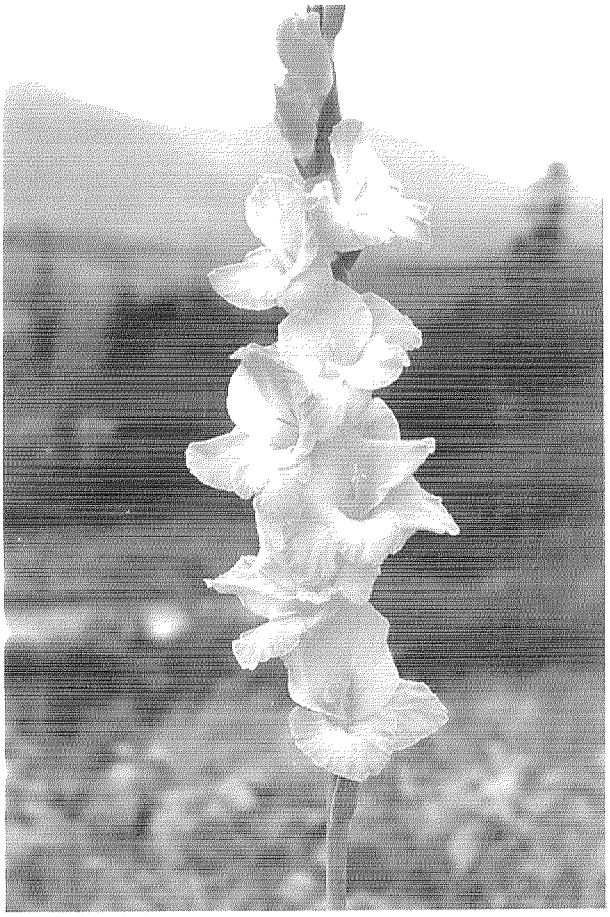
Figure 3:
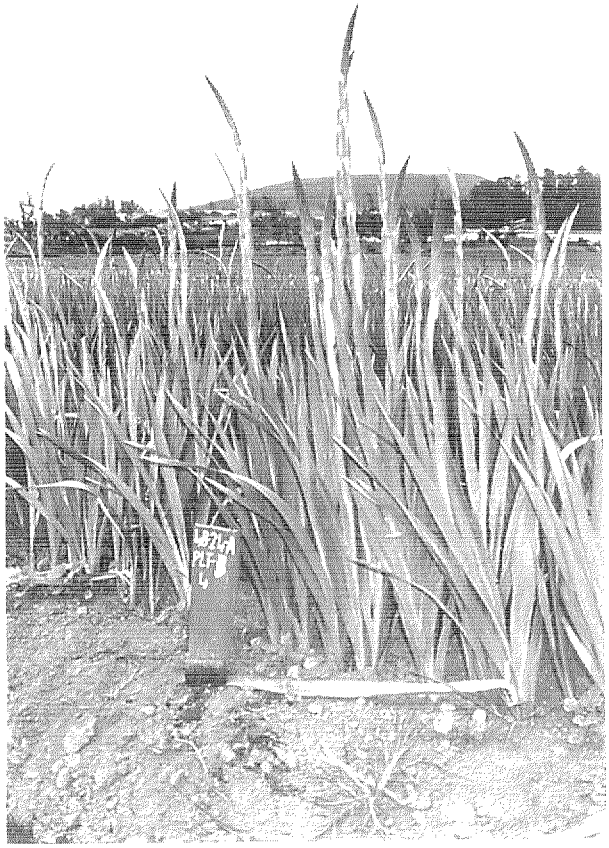
FIG. 3 is a photograph of the 'Princess Lee' variety plant prior to blooming.
Figure 4:
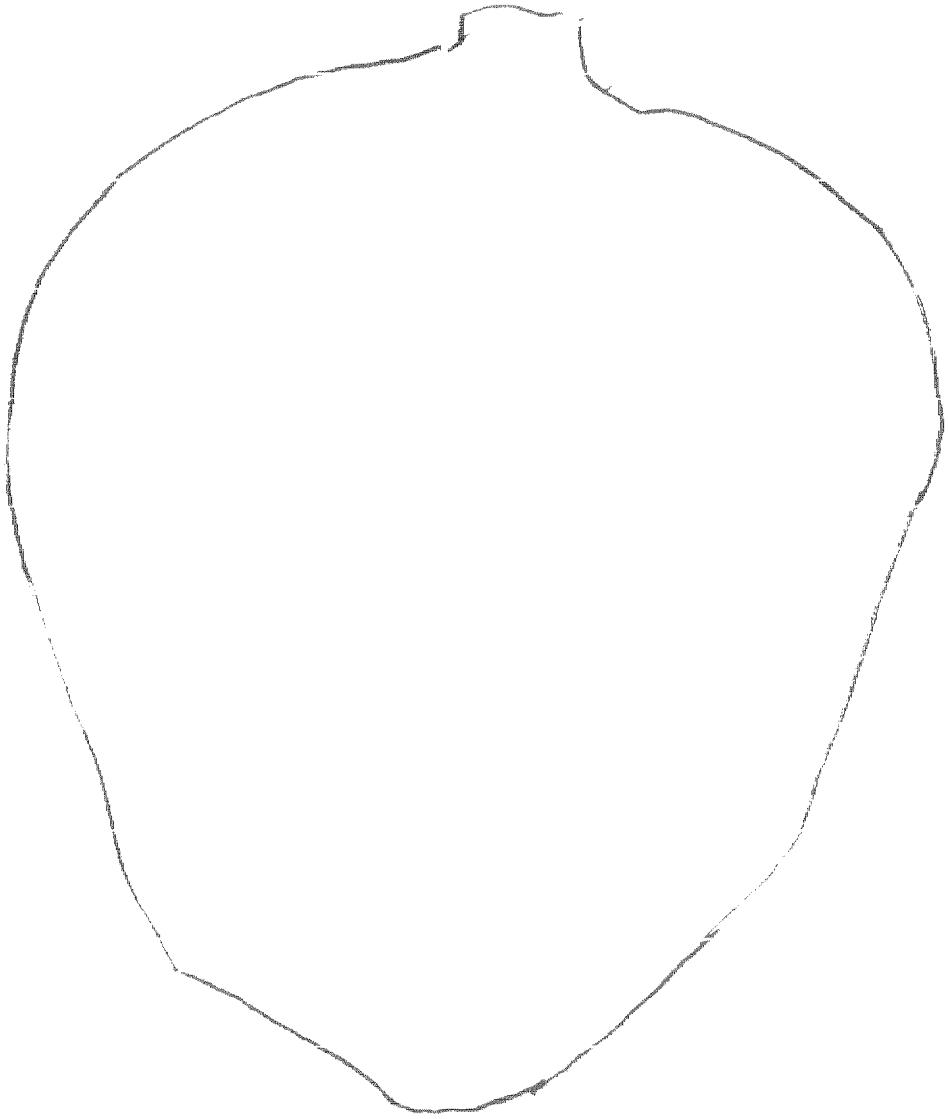
FIG. 4 is a drawing illustrating the shape and size of the large petals.

The bud size of the 'Princess Lee' variety is about 7 cm in length. In all blooms reviewed, the flowers of the variety each consist of a total of six petals, with the large petals located in the upper half of the bloom, and the smaller petals located in the lower half of the bloom. For example, the most common petal arrangement consists of three large petals, one medium-sized petal, and two small petals. Here, the large petals are oriented in the upper half of the flower, located between 9:00 and 3:00 on a clock face. The medium petal is located in the lower half of the flower between 4:00 and 8:00, and the two small petals are typically found between 3:30 and 9:00 on the lower half of the flower. In a second arrangement, the flower consists of three large petals, two medium-sized petals, and one small petal. As in the first arrangement described above, the large petals are positioned in the upper half of the bloom, and the medium and small petals are oriented on the lower half of the bloom. In a third petal arrangement of the variety, the flower consists of one large petal at 1:00, four medium petals between 2:00 and 7:00, and a small petal near 6:00. Finally, in a fourth arrangement, the flower consists of two large petals positioned on the upper half of the bloom (between 9:00 and 3:00), two medium-sized petals positioned on the lower half of the bloom between 3:00 and 9:00 , and two small petals in the lower half of the bloom. FIG. 4 illustrates the shape and size of the large petals. The diameter of the entire bloom is about 12 cm.

The color of the corolla bloom tight is Red Group 41B. The color of the bloom open perfect condition is Red Group 52D for the majority of the petal. The outer margin of the petal is Red Group 48C when observed in south Florida (note that the color here is several shades darker in when observed in Holland). The color the bloom open going down is Red Group 50C. The color of the bloom deep within the throat is Red Group 48B.

The variety has three stamens and one pistil. The color of the pistil head is White Group N155D with a touch of color Red Group 49D on the tips. The color of the pistil stem is White Group N155B. The color of the stamen head is Green White Group 157A on the backside with small amounts of Red Purple 70B on the front side. The color of the stamen stem is White Group N155B.

The corms of the 'Princess Lee' variety are typical for the gladiolus and have a Yellow Orange Group 14B color under the husk on the top of the bulb one day after harvest.

GENERAL OBSERVATIONS

The 'Princess Lee' is a true pink gladiolus variety having very straight, strong stems, a large bloom size (i.e. 12 cm diameter), medium resistance to Fusarium and Curvalaria fungal species and other foliar diseases, and good resistance to attack by insects.

The 'Princess Lee' variety takes about 90 days after planting to produce the first bloom when grown in Ecuador. The variety is slow to open in that it will take three to three and one half days to open the first bloom after being placed in water, compared to only one to two days for other fast opening varieties. Consequently, the 'Princess Lee' variety should be harvested with three to four flowers showing color. The 'Princess Lee' variety can hold seven blooms open simultaneously in a vase of water after harvest from a tight cut stem. The total duration of blooming is about eleven days.

The variety does not emit a fragrance.

Compared to the male parent 'White Prosperity' (the variety most similar to the 'Princess Lee'), the 'Princess Lee' variety produces a heavier stem that is 8 to 10 cm longer and has six to eight more blooms. Both varieties (i.e. 'White Prosperty' and 'Princess Lee') prefer the long days of summer; however, the 'Princess Lee' variety also has the ability to grow in short days as opposed to the 'White Prosperity' variety, which obtains a length that is too short to be economically feasible when grown during shorter day-length days. The bloom size of the 'Princess Lee' variety is about 2 cm larger in diameter compared to the bloom size of the 'White Prosperity'. Both the 'Princess Lee' and 'White Prosperity' varieties are resistant to burning in the hot summer sun.

Compared to the female parent 'Dr. Magie', the 'Princess Lee' variety has a larger stem diameter by approximately 0.3 cm, a spike that is at least 30 cm longer, and a flower diameter that is about 2–3 cm larger. The stem of 'Princess Lee' variety also holds about eight more blooms than the 'Dr. Magie' variety.

I claim:

1. A new and distinct gladiolus variety of plant 'Princess Lee', as shown and described herein.

* * * * *